United States Patent
Babula et al.

(10) Patent No.: US 7,698,241 B2
(45) Date of Patent: Apr. 13, 2010

(54) METHOD FOR RESOLVING CONDITIONS OF A MEDICAL SYSTEM USING SOLUTION VERIFICATION

(75) Inventors: Deborah Ann Babula, Franklin, WI (US); Michael Allan Clawson, Genoa City, WI (US)

(73) Assignee: General Electric Company, Schenectady, NY (US)

( * ) Notice: Subject to any disclaimer, the term of this patent is extended or adjusted under 35 U.S.C. 154(b) by 198 days.

(21) Appl. No.: 11/312,796

(22) Filed: Dec. 20, 2005

(65) Prior Publication Data

US 2007/0143237 A1    Jun. 21, 2007

(51) Int. Cl.
*G06N 5/00* (2006.01)
*G06N 5/04* (2006.01)

(52) U.S. Cl. .............................. 706/45; 706/46; 706/47
(58) Field of Classification Search .................. 706/45, 706/46, 12; 705/2
See application file for complete search history.

(56) References Cited

U.S. PATENT DOCUMENTS

| 6,509,914 | B1 * | 1/2003 | Babula et al. | 715/762 |
| 7,225,406 | B2 * | 5/2007 | Babula et al. | 715/736 |
| 2003/0061071 | A1 * | 3/2003 | Babula et al. | 705/2 |

* cited by examiner

*Primary Examiner*—David R Vincent
*Assistant Examiner*—Adrian L Kennedy
(74) *Attorney, Agent, or Firm*—Fletcher Yoder

(57) ABSTRACT

A technique is provided for resolving a reportable condition. Upon detection of a reportable condition on a processor-based medical system, machine data is provided to a knowledge engine. One or more identified solutions are received from the knowledge engine and implemented on the processor-based medical system. The one or more solutions are verified as they are implemented to determine if the currently implemented solution resolves the reportable condition. Routines implementing some or all of the technique may be provided on a processor-based system or on a machine-readable medium.

12 Claims, 2 Drawing Sheets

METHOD FOR RESOLVING CONDITIONS OF A MEDICAL SYSTEM USING SOLUTION VERIFICATION

BACKGROUND

Figure 1:
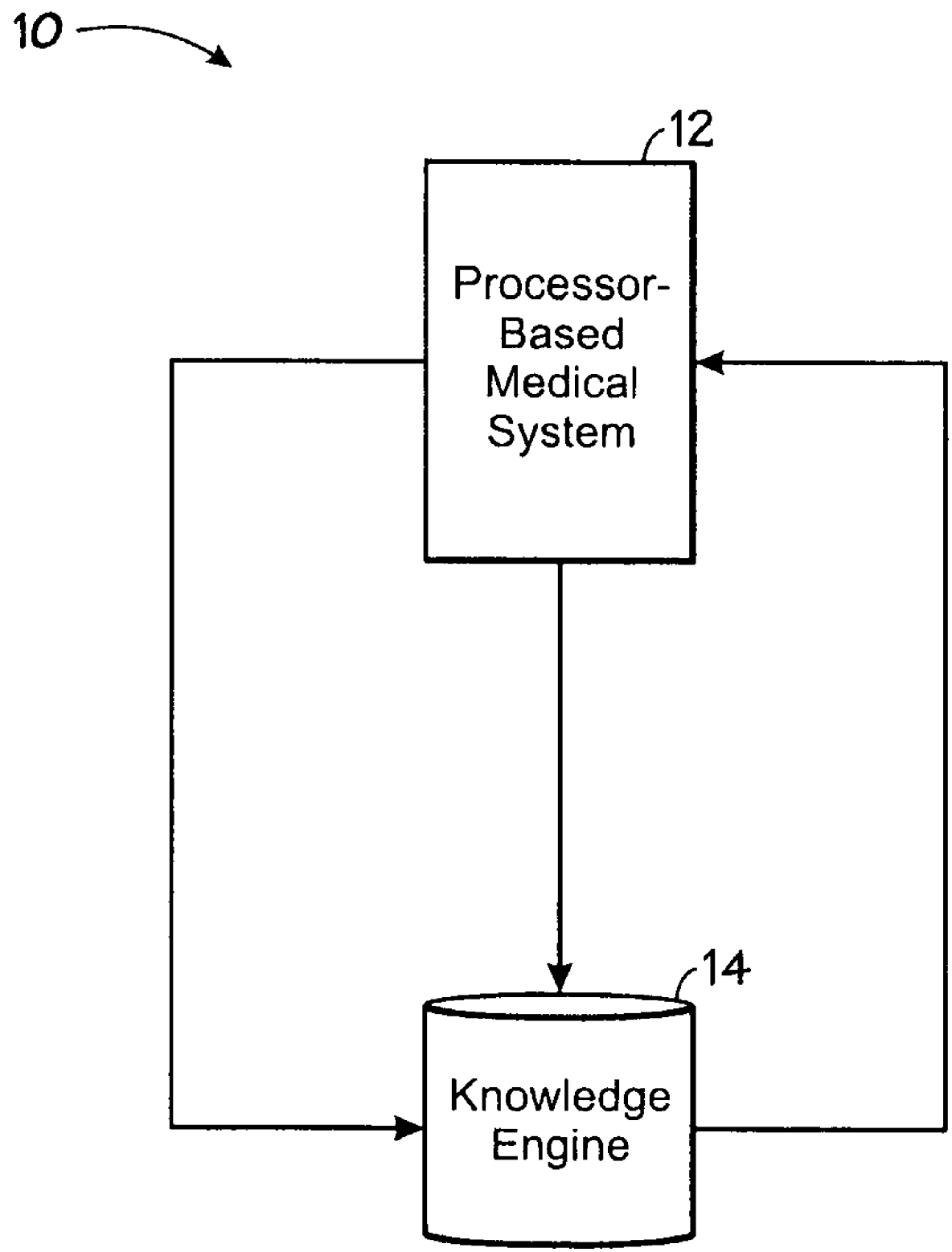

The invention relates generally to providing remote service assistance in an automated or semi-automated manner, such as by automatically providing service suggestions which may be automatically implemented or implemented by a customer without on-site assistance.

In a variety of industrial, commercial, medical, and research contexts, various pieces of equipment may be employed on a day-to-day basis to accomplish or facilitate the work being performed at a facility. In many instances, the facility may rely upon a third party to provide service for some or all of the equipment at the site to ensure that the equipment remains operational and available. For example, in an industrial setting, production equipment or computer resources that are in operation in a continuous or near continuous manner may be serviced by an off-site party that provides servicing as needed or requested. Similarly, hospitals, clinics, and research facilities may utilize another party to service some or all of the diagnostic, monitoring, and/or imaging equipment at a site so that the equipment remains available where and when it is needed.

Such an arrangement, however, may impose burdens on the service provider that are difficult to overcome in an efficient and cost effective manner. For example, a service provider may utilize field personnel, such as field engineers, to provide on-site support to a variety of clients. As one might expect, such on-site support is resource and time intensive, requiring highly trained personnel to travel to various customer sites to provide support. As a result, support time is lost to travel, and other factors associated with maintaining field personnel and services. Furthermore, the customer experiences downtime due to system problems that, in some cases, can be addressed without the aid of a field engineer, such as by the customer implementing the fix themselves.

In many instances, a problem being experienced at a client site may be diagnosed based on information, such as error logs or messages, available at the site. In such instances, one or more solutions or fixes to the problem may be indicated. Depending on the problem, implementing such fixes may not require the technical expertise or experience of a field engineer or technician. In such instances, it may be undesirable to provide a costly and time-consuming on-site service call.

BRIEF DESCRIPTION

A method is provided for resolving a reportable condition. The method includes the step of providing machine data to a knowledge engine upon detection of a reportable condition on a processor-based medical system. One or more identified solutions are received and provided to an operator of the processor-based medical system to implement.

A method is provided for diagnosing a reportable condition. The method includes the step of receiving machine data from a processor-based medical system upon detection of a reportable condition on the processor-based medical system. One or more solutions to the reportable condition are identified in a knowledge engine based on the machine data. The one or more solutions are provided to the processor-based medical system. The knowledge engine is updated based on the success or failure of at least one of the one or more identified solutions at resolving the reportable condition.

One or more machine-readable media are provided in accordance with embodiments of the present technique. The one or more machine-readable media include a routine configured to receive machine data from a processor-based medical system upon detection of a reportable condition on the processor-based medical system. The one or more machine-readable media also include a routine configured to identify one or more solutions to the reportable condition in a knowledge engine based on the machine data. A routine is also included which is configured to provide the one or more solutions to the processor-based medical system. In addition, a routine is include which is configured to update the knowledge engine based on the success or failure of at least one of the one or more identified solutions at resolving the reportable condition.

A processor-based medical system is provided in accordance with embodiments of the present technique. The processor-based medical system includes a processor configured to execute routines adapted to provide machine data to a knowledge engine upon detection of a reportable condition on the processor-based medical system. The processor is also configured to execute routines adapted to receive one or more identified solutions and to provide the one or more identified solutions to an operator of the processor-based medical system to implement.

A knowledge engine is provided in accordance with embodiments of the present technique. The knowledge engine includes a database configured to be searched using machine data generated in response to a reportable condition on a processor-based medical system to identify one or more solutions to the reportable condition. The knowledge engine is also configured to provide the one or more solutions to the processor-based medical system. In addition, the knowledge engine is configured to be updated based on the success or failure of at least one of the one or more identified solutions at resolving the reportable condition.

DRAWINGS

Figure 2:
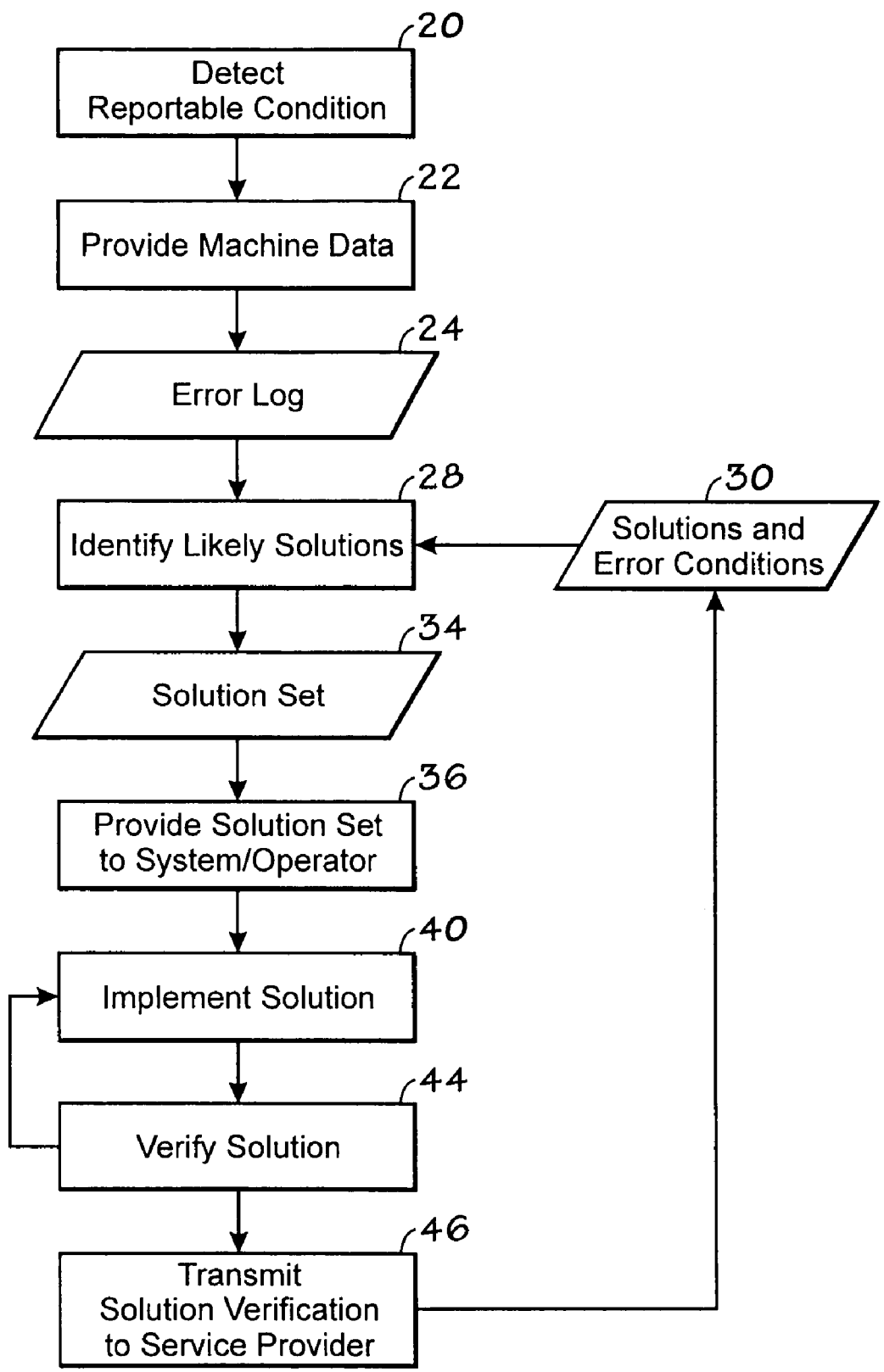

These and other features, aspects, and advantages of the present invention will become better understood when the following detailed description is read with reference to the accompanying drawings in which like characters represent like parts throughout the drawings, wherein:

FIG. 1 depicts an exemplary system for use in accordance with the present technique; and FIG. 2 depicts a flowchart depicting exemplary steps in accordance with the present technique.

DETAILED DESCRIPTION

The present technique provides an automated or semi-automated technique for addressing errors or system problems at a client site. In particular, the present technique identifies solutions in response to a problem reported by a system at the client site. The solutions may be implemented by an operator or user at the client site, i.e., by the client themselves, without the assistance of a field engineer or technician. In addition, successful implementation of a solution may update the solution identification process, facilitating future diagnoses, and/or the system design processes, leading to design improvements.

Referring now to FIG. 1, an exemplary error-correction system 10 for use in conjunction with the present technique is depicted. In one embodiment, the exemplary error correction system 10 includes a processor-based medical system 12. Such processor-based medical systems 12 may include a variety of medical systems incorporating microprocessors or general- or specific-purpose computer systems that executes various routines and processing functions of the system 10. For example, a microprocessor component of the system 12 may execute various operating system instructions as well as software routines stored locally or remotely from the system 12. In addition, such a microprocessor component may process data provided as inputs for various routines or software programs, such as data provided as part of the present technique in computer-based implementations.

For example, the processor-based medical system 12 may include imaging or diagnostic scanners, such as ultrasound systems, X-ray based imaging systems, computed tomography (CT) systems, positron emission tomography (PET) systems, mammography systems, and so forth. Similarly, the processor-based medical system 12 may include other diagnostic or evaluative systems or support systems, such as picture archiving systems (PACS) or other archival systems, patient monitoring systems, medical record or information systems, and so forth. In other embodiments, the processor-based system is not medical in nature but may be an industrial and/or commercial device incorporating some level of processor-based functionality. For example, commercial and/or industrial security and screening systems, manufacturing systems, quality control systems, sales devices, and so forth, are systems that might incorporate processor-based functionality in accordance with the present technique.

The exemplary error correction system 10 also includes a knowledge engine 14, which may be provided as a problem solution database or other searchable data store. In the depicted embodiment, the knowledge engine 14 is in continuous or intermittent communication with the processor-based medical system 12. For example, in some embodiments, the knowledge engine 14 is provided as a searchable database on a memory component (such as a hard drive, optical disk, or other memory component) of the processor-based medical system 12. In other embodiments, the knowledge engine 14 is remote from the processor-based medical system 12, with communication between the processor-based medical system 12 and the knowledge engine 14 being accomplished over a network, such as the Internet or a hospital local area network, or via a direct, non-network communication connection. Communication may be accomplished via suitable wire or wireless network adapters, via modem, or via other suitable communication interface devices.

In one embodiment of the present technique, the exemplary processor-based medical system 12 is configured to communicate with the knowledge engine 14 in the event of an error or other event deemed to be reportable. In one embodiment, processor-based medical system 12 communicates with the knowledge engine 14 when an event occurs which is addressable or correctable by on-site personnel (i.e., system operators or other client personnel), but for which a field engineer or technician might otherwise be contacted. Referring now to FIG. 2, exemplary steps (some or all of which may be executed by the exemplary processor-based system 12 and/or knowledge engine 14) for addressing such reportable conditions are provided. Some or all of the steps may be performed as part of a software or a database based application. Alternatively, application specific hardware or circuitry configured to perform some or all of the steps may be utilized.

As depicted in FIG. 2, a reportable condition is detected (block 20) in the processor-based medical system 12. Such a reportable condition may be a system error or failure, an abnormal or unexpected operating condition, or any other condition or event that triggers operator intervention or attention. Upon detection of such a condition at block 20, relevant machine data is provided (block 22) to the knowledge engine 14. The machine data may include error logs 24 (as depicted) or other operational or configuration data for the processor-based medical system 12. Likewise, the machine data may include error codes or other indicators associated with the triggering event.

Based on the provided machine data, the knowledge engine 14 may identify likely solutions (block 28) from among a set of problems and solutions 30 that are searchable by the transmitted data, here error log 24. In one embodiment, only those solutions are identified that can be implemented by the system operator or by other client personnel at the customer site, i.e., without the aid of a field technician or engineer. For example, the set of searchable solutions 30 may include solutions that are relevant or applicable to particular entries in an error log 24 or to particular error codes and so forth. In addition, the set of searchable solutions 30 may include other information associated with various combinations of errors and solutions, such as the likelihood that a solution will resolve a problem, and so forth. In this way, one or more possible solutions 34 to the problem may be identified and, where more than one solution is identified, a priority or ranking may be provided with the identified solutions 34 indicating the order in which the solutions are to be implemented. In addition, the set of identified solutions may be configured, by the knowledge engine 14 or the operator of the system 12, such that all of the identified solutions may be provided or only a subset. For example, a subset may be limited to provide only the first five, ten, or twenty solutions, and so forth. Similarly, a subset may be limited to provide only those solutions with a likelihood of success greater than a set threshold, such as greater than a 10%, 25%, 50% and so forth, likelihood of success.

The identified solutions 34 are provided (block 36) to the processor-based system 12 and/or to an operator of the system 12 to be implemented (block 40). In one embodiment, an operator at the system 12 implements one or more of the identified solutions 34 until the triggering event or problem is resolved. For example, the identified solutions may be displayed at the system 12 or another system that the operator (such as a customer or other client site employee) has access to. The operator may then implement the solutions in the displayed order without contacting or calling in a field or service engineer. In another embodiment, the processor-based system 12 itself may automatically implement one or more of the identified solutions 34 until the triggering event or problem is resolved. The identified solutions 34 are implemented until the problem or triggering event is resolved or no identified solutions remain to be implemented.

Each implemented solution is verified (block 44), automatically or by an operator of the system 12, to determine whether the problem or triggering event is resolved by the currently implemented identified solution 34. If a solution is successfully verified, the success of the solution may be transmitted (block 46) to a service provider to update the knowledge engine 14 in question or a master knowledge engine. Likewise, information about unsuccessful solutions may also be transmitted to the service provider and used to update the knowledge engine 14. In this way, future performance of the knowledge engine 14 may be updated to reflect the success or lack of success of solutions identified for a given problem, such as in the solution identification or prioritization operations of the knowledge engine 14. In addition, the service provider may use such verification information in design and redesign efforts associated with the processor-based medical system 12. In this way, reliability of existing and future versions of the system 12 may be improved.

By the present technique, customer support may be facilitated by providing timely fixes to an operator that the operator can implement herself, without the aid of a field support person. In addition, system fixes may be facilitated where remote fixes would be possible except for a lack of connectivity, especially where the knowledge engine 14 is local to the system 12. Likewise, fixes may be facilitated where a manual or physical task or manipulation constitutes part of the solution, but it is a task or manipulation that can be performed by the customer.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for resolving a reportable condition of a medical system comprising:

automatically providing machine data representing a reportable condition to a rule-based knowledge engine that is searchable by the machine data without human intervention through event submission instructions implemented on a processor-based medical system upon detection of a reportable condition detected though detection instructions implemented on the processor-based medical system;

receiving one or more identified solutions through receiving instructions implemented on the processor-based medical system;

implementing the one or more identified solutions through implementation instructions implemented on the processor-based medical system;

automatically verifying, through resolution verification instructions implemented on the processor-based medical system, the one or more solutions without human intervention as they are implemented to determine if the currently implemented solution resolves the reportable condition; and automatically providing the verification results for the reported condition to the knowledge engine, wherein the verification results include the detected condition, the implemented solution, and whether the solution was successful.

2. The method of claim 1:

wherein implementing the one or more identified solutions occurs automatically without human intervention.

3. The method of claim 1, wherein the machine data comprises at least one of an error log, error codes, operational data, or configuration data for the processor-based medical system.

4. The method of claim 1, wherein the processor-based medical system comprises at least one of an imaging system, an archival system, a record storage and retrieval system, or a patient monitoring system.

5. The method of claim 1, comprising providing information about the success or failure of at least one of the one or more identified solutions at resolving the reportable condition to the knowledge engine.

6. A processor-based medical system, comprising:

a processor configured to execute routines adapted to automatically provide uniform machine data representing the verified results of a reportable condition to a knowledge engine that is searchable by the machine data without human intervention upon detection of a reportable condition found through implementation of detection instructions on the processor-based medical system, to receive one or more identified solutions in an order based on likelihood of success through implementation of receiving instructions on the processor-based medical system, and to provide the one or more identified solutions to the processor-based medical system to implement without human intervention through implementation of implementation instructions on the processor-based medical system and wherein the verified results include the detected condition, the implemented solution and whether the solution was successful.

7. The processor-based medical system of claim 6, wherein the processor is configured to execute routines adapted to verify the one or more solutions as they are implemented to determine if the currently implemented solution resolves the reportable condition.

8. The processor-based medical system of claim 6, wherein the machine data comprises at least one of an error log, error codes, operational data, or configuration data for the processor-based medical system.

9. The processor-based medical system of claim 6, wherein the processor-based system comprises at least one of an imaging system, an archival system, a record storage and retrieval system, or a patient monitoring system.

10. The processor-based medical system of claim 6, wherein the knowledge engine is local to the processor-based medical system.

11. The processor-based medical system of claim 6, wherein the knowledge engine is remote from the processor-based medical system.

12. The method of claim 1, wherein the knowledge engine, when searched, provides the one or more solutions to the processor-based medical system in an order based on likelihood of success as determined based on previous success and failure feedback, and wherein the knowledge engine is automatically updated without human intervention based on the success or failure of at least one of the one or more identified solutions at resolving the reportable condition through results provided to the knowledge engine by the processor-based medical system reporting the condition.

* * * * *